United States Patent
Riitano

[19]

[11] Patent Number: 6,079,979
[45] Date of Patent: Jun. 27, 2000

[54] ENDONONTIC IRRIGATOR TIPS AND KITS

[75] Inventor: Francesco Riitano, Soverato, Italy

[73] Assignee: Ultradent Products, Inc., South Jordan, Utah

[21] Appl. No.: 09/014,764

[22] Filed: Jan. 28, 1998

[51] Int. Cl.[7] .................................................. A61G 1/00
[52] U.S. Cl. .......................................... 433/81; 433/224
[58] Field of Search .............................. 433/80, 81, 102, 433/224, 90

[56] References Cited

U.S. PATENT DOCUMENTS

| | | | |
|---|---|---|---|
| 3,221,409 | 12/1965 | Thiel et al. | 32/60 |
| 3,713,221 | 1/1973 | Malmin | 32/57 |
| 4,048,723 | 9/1977 | Thorup | 32/40 |
| 4,236,889 | 12/1980 | Wright | 433/86 |
| 4,248,589 | 2/1981 | Lewis | 433/80 |
| 4,249,899 | 2/1981 | Davis | 433/32 |
| 4,276,880 | 7/1981 | Malmin | 128/221 |
| 4,512,769 | 4/1985 | Kozam et al. | 604/209 |
| 4,531,912 | 7/1985 | Scjiss et al. | 433/80 |
| 4,619,612 | 10/1986 | Weber et al. | 433/80 |
| 4,676,749 | 6/1987 | Mabille | 433/88 |
| 4,787,845 | 11/1988 | Valentine | 433/88 |
| 4,820,152 | 4/1989 | Warrin et al. | 433/86 |
| 4,872,837 | 10/1989 | Issalene et al. | 433/29 |
| 4,907,968 | 3/1990 | Eisner et al. | 433/80 |
| 4,942,870 | 7/1990 | Damien | 128/66 |
| 4,950,160 | 8/1990 | Karst | 433/88 |
| 4,958,751 | 9/1990 | Curtis et al. | 222/192 |
| 4,975,054 | 12/1990 | Esrock | 433/80 |
| 4,984,984 | 1/1991 | Esrock | 433/80 |
| 4,993,941 | 2/1991 | Maita et al. | 433/80 |
| 5,033,961 | 7/1991 | Kandler et al. | 433/89 |
| 5,049,071 | 9/1991 | Davis et al. | 433/80 |
| 5,067,899 | 11/1991 | Paschal | 433/80 |
| 5,127,831 | 7/1992 | Bab | 433/80 |
| 5,147,203 | 9/1992 | Seodemberg | 433/29 |
| 5,188,617 | 2/1993 | Linder | 604/232 |
| 5,192,206 | 3/1993 | Davis et al. | 433/80 |
| 5,197,875 | 3/1993 | Nerli | 433/80 |
| 5,218,956 | 6/1993 | Handler et al. | 128/66 |
| 5,236,355 | 8/1993 | Brizzolars et al. | 433/80 |
| 5,236,356 | 8/1993 | Davis et al. | 433/80 |
| 5,242,300 | 9/1993 | Esrock | 433/80 |
| 5,273,428 | 12/1993 | Fischer | 433/80 |
| 5,286,201 | 2/1994 | Yu | 433/80 |
| 5,295,827 | 3/1994 | Fundingsland et al. | 433/80 |
| 5,297,962 | 3/1994 | O'Connor et al. | 433/89 |
| 5,306,146 | 4/1994 | Davis et al. | 433/80 |
| 5,342,195 | 8/1994 | Davis et al. | 433/80 |
| 5,460,619 | 10/1995 | Esrock | 604/280 |
| 5,468,148 | 11/1995 | Ricks | 433/80 |
| 5,474,450 | 12/1995 | Chronister | 433/80 |
| 5,490,779 | 2/1996 | Malmin | 433/81 |
| 5,558,518 | 9/1996 | Bab et al. | 433/80 |
| 5,570,709 | 11/1996 | Haddad et al. | 132/322 |
| 5,622,498 | 4/1997 | Brizzolara et al. | 433/80 |
| 5,626,473 | 5/1997 | Muhibauer et al. | 433/89 |
| 5,882,196 | 3/1999 | Kert | 433/81 |

OTHER PUBLICATIONS

Ultradent Materials and Procedures Manual, Illustration of Irrigation Tips, p. 89, 1996.

*Primary Examiner*—Nicholas D. Lucchesi
*Attorney, Agent, or Firm*—Workman, Nydegger, Seeley

[57] ABSTRACT

An endodontic irrigator tip includes a hub and a cannula coupled to the hub. The hub includes a neck having a distal stop end which ensheathes the proximal portion of the cannula. The distal stop end is angled with respect to the longitudinal axis of the hub. The stop end prevents the insertion of the cannula beyond a desired distance, thereby preventing perforation of the apex of the root canal. The stop end has a substantially greater diameter than the diameter of the cannula Thus, the stop end of the neck rests on the occlusal surface of the crown of the tooth while the cannula extends the desired distance within the root canal.

29 Claims, 7 Drawing Sheets

6,079,979

ENDONONTIC IRRIGATOR TIPS AND KITS

BACKGROUND OF THE INVENTION

1. The Field of the Invention

This invention is in the field of instruments for use in medicine and dentistry. More specifically, this invention is in the field of endodontic irrigator tips for irrigating root canals as part of a root canal procedure.

2. The Relevant Technology

To preserve a tooth that has a diseased pulp cavity, it is necessary to prevent bacterial proliferation within the pulp canal of the tooth by removing the diseased or necrotic pulp material from the pulp canal. After the pulp material has been removed or extirpated from a tooth, the pulp cavity is typically filled or obturated with a material such as gutta percha to occlude the pulp cavity and a sealer to seal the pulp cavity. This procedure is referred to as root canal therapy. Root canal cleaning is generally achieved by hand or mechanical instrumentation with files that are configured to bore and cut.

It is also common during the root canal procedure to irrigate a pulp cavity and the various root canals involved using an endodontic irrigator tip. Irrigation assists in removing debris and necrotic material cut by the endodontic files and bores. Disinfecting solutions can also be employed in irrigation, thereby disinfecting the pulp cavity and root canals during the operative procedure.

In addition to being thin and tight, root canals are often twisted and cumbersome to negotiate. In order to place irrigator tips at a convenient angle within a tooth and negotiate the convoluted passages of root canals, irrigator tips are typically bent. U.S. Pat. No. 4,993,941 to Maita et al., for example, discloses a dental irrigator needle having a selectively angled cannula which was designed to provide more convenient fluid delivery.

The problem with this design, however, is that the needle itself is bent, which will potentially crimp a small, delicate root canal cannula. While it is possible to bend a larger diameter cannula without kinking or preventing the flow of the irrigation fluid therethrough, smaller diameter cannulas, which are particularly useful in tight root canal areas, are subject to crimping and breakage when bent. The problems associated with crimping of the cannula are particularly acute when thin, delicate irrigator tips are involved.

Another problem associated with root canal therapy is apical perforation. Before a file or irrigation tip is inserted into a root canal, the length of the root canal is determined to identify a suitable working length for the file or irrigation tip. Generally, the working length corresponds to the distance from a fixed reference position on the crown of a tooth to a location above the apical constriction of the root canal. Radiography is the most common method for measuring the length of the root canal. The preoperative x-ray image of the diseased tooth is taken from the front or back of the tooth as depicted in FIG. 1 to show a cross-sectional view of the root canals 12 of tooth 10. The length of the root canal and the desired working length of the cannula to be placed therein is then determined.

Perforation of the apex 14 of a root canal 12 can result from the use of files or endodontic irrigation tips which are too long. Such apical perforations typically result from an error in estimating the length of a root canal or the working length of the cannula Similarly, apex 14 can be perforated by extrusion of infected material through the apex due to the force exerted by the file or tip on the material as the file or tip is pushed downward to reach the apex. In addition to exposing the tissue surrounding the tooth to the infected material, apical perforations also substantially complicate subsequent healing of the root canal.

The possibility of perforating the apex is particularly frustrating because it is often desirable to deliver fluid which reaches the apex in order to disinfect the apex and dissolve necrotic tissue therein. However, certain fluids are too viscous to reach the apex if delivered too far above the apex. Sodium hypochlorite, for example, is a widely used, strong disinfectant that is viscous and can stick in the pulp chamber rather than reaching the apex if not delivered with precision from the appropriate location above the apex. Attempts to deliver the solution from the appropriate location, however, may result in the perforation of the apex.

Practitioners have made some attempts to place irrigator tips within teeth without perforating the apex. The working length of endodontic irrigator tips is sometimes limited by (i) bending the tips to prevent them from extending too far into a root canal, or (ii) marking the tips with a pen at a location on the tips which should not extend past the rim of the crown. The problem with each of these approaches, however, is that they are unreliable, and can contaminate the tip as a result of the handling of the tip prior to use. In addition, bending a cannula can crimp or kink the cannula.

The possibility of perforating the apex of the root canal with an endodontic file is sometimes prevented by employing a removable stop which is placed about the distal insertion end of the file and pushed a desired distance toward the proximal gripping end of the file. Such adjustable stops, however, are prone to slip and slide along the longitudinal axis of the file, thereby allowing perforation of the apex. In addition, placing a stop on the file requires handling of the file prior to use, possibly contaminating the file.

Irrigating probes used for other dental applications also fail to solve the problems associated with typical endodontic irrigation probes. For example, U.S. Pat. No. 5,127,831 to Bab discloses a flexible end irrigation probe which is designed for irrigating periodontal pockets. The design features an irrigator having a smooth transition between a flexible plastic distal end and a more rigid arm which extends from the hub. This smooth transition is important to the design because the irrigator is configured to achieve atraumatic nonsensitizing penetration into periodontal pockets. The Bab device would not be desirable for root canal therapy because the smooth transition of the Bab irrigation probe fails to provide a stopping mechanism which would prevent the irrigator from extending beyond a desired distance.

Another problem associated with the cannulas of typical endodontic irrigator tips is that it is sometimes desirable to be able to gently press the tip of a cannula through tissue in order to reach the area in which irrigation is desired. Typical orifices, however, are subject to being clogged by the tissue during this process. Furthermore, typical orifices can sometimes spray the irrigating fluid with too great of force directly into a particular location. Finally, certain cannulas are too obtrusive to root canal surfaces or are inefficient to manufacture.

There is therefore a need within the art for an endodontic irrigator tip having a cannula that can be conveniently used without crimping and without risk of apical perforation. There is also a need within the art for different irrigator tips which can be used to buffer the impact of liquid delivered into a root canal, extend a cannula through a tissue in order to reach a desired irrigating area, prevent the manipulation of root canal surfaces, or are efficient to manufacture.

SUMMARY AND OBJECTS OF THE INVENTION

It is therefore an object of the invention to provide an improved endodontic irrigator tip.

It is another object of the invention to provide an endodontic irrigator tip having an angled portion which does not kink a cannula associated with the irrigator tip.

It is another object of the invention to provide an endodontic irrigator tip which features a stop for preventing the placement of the irrigator tip past a desired location.

It is another object of the invention to provide improved insertion ends of irrigator tips.

It is another object of the invention to provide kits featuring irrigation tips, such as tips having cannulas with a variety of different working lengths, thereby enabling the practitioner to treat root canals of varying sizes.

The endodontic irrigator tip of the present invention comprises a hub coupled to a cannula. The hub has a body having a proximal end adapted for coupling to a fluid delivery means, such as a syringe. The hub also has a neck having a proximal end coupled to the distal end of the body. The neck has an integral distal stop end for preventing the placement of the irrigator tip past a desired location. A hollow chamber is located in the hub which is defined by an interior surface. The hollow chamber extends through the body and the neck and has an inlet such that fluid can be received from a syringe.

The cannula has a distal insertion end and a proximal end sheathed within the distal stop end of the neck. Thus, a portion of the cannula extends from the stop end of the neck with sufficient length to extend into a root canal of a tooth. An interior surface of the cannula defines a conduit in fluid communication with the hollow chamber. The cannula has an orifice located at the distal insertion end thereof.

In one embodiment, the distal stop end of the neck is angled with respect to the longitudinal axis of the body. The cannula sheathed within the distal stop end is substantially straight. As a result, the cannula is angled with respect to the longitudinal axis of the body, but the cannula is not subject to being crimped when the cannula is moved within the range of motion that is necessary to move a cannula during root canal therapy. The irrigator tip is therefore convenient for the practitioner to place within the mouth of the patient, yet avoids the possibility of crimping the cannula.

The stop end of the neck is sufficiently rigid to ensure that the portion of the cannula sheathed within the stop end remains substantially straight. Thus, the rigidity of the neck also prevents the crimping of the cannula. The neck is also rigid in order to enable the practitioner to guide the cannula into a desired location within a root canal. Preferably, the cannula is flexible enough to negotiate the angles of the root canal. The distal stop end of the neck has a diameter that is substantially greater than the outer diameter of the cannula, such that the stop end acts as an integral stop to prevent penetration into a root canal by the endodontic irrigator tip beyond the length of the portion of the cannula extending from the stop end of the neck.

The invention also relates to a kit which includes irrigator tips having cannulas with different working lengths. Each working length is preset to fit into a root canal having a different length. Because of the integral stop end of the neck, the practitioner is not required to place a stop on the cannula. Instead, the practitioner selects an irrigator tip having a preset cannula length and the integral stop end of the neck prevents the cannula from extending beyond a desired distance into the root canal. This prevents the potential contamination associated with handling the tip while placing a typical removable stop thereon and assures that the stop indicator does not move.

The distal insertion end of the cannula may comprise a variety of different tips. In one embodiment, the tips include sharp ends for extending the cannula through tissue in the root canal in order to reach a desired irrigating area. Optionally, the tips are designed to prevent manipulation of the surfaces of a root canal. Orifices which allow liquid to flow from the cannula may optionally be located on the side of the cannula to buffer the impact of the flow of the liquid, preventing apical perforation.

These and other objects and features of the present invention will become more fully apparent from the following description and appended claims, or may be learned by the practice of the invention as set forth hereinafter.

BRIEF DESCRIPTION OF THE DRAWINGS

In order that the manner in which the above-recited and other advantages and objects of the invention are obtained, a more particular description of the invention briefly described above will be rendered by reference to a specific embodiment thereof which is illustrated in the appended drawings. Understanding that these drawings depict only a typical embodiment of the invention and are not therefore to be considered to be limiting of its scope, the invention will be described and explained with additional specificity and detail through the use of the accompanying drawings in which.

DETAILED DESCRIPTION OF THE PREFERRED EMBODIMENTS

Figure 1:
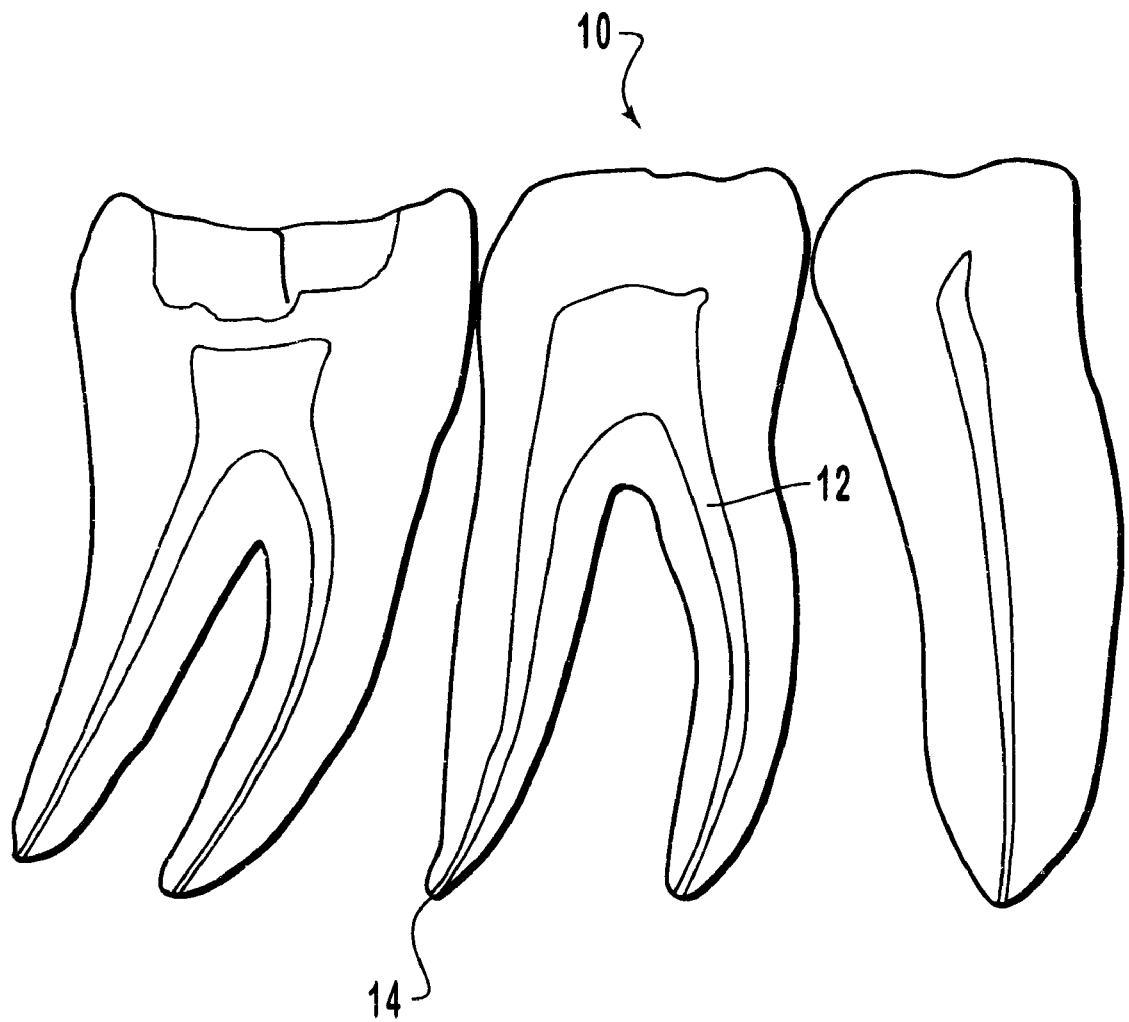
FIG. 1 is a depiction of a preoperative x-ray image of a series of diseased teeth taken in order to determine the working length of an endodontic file or irrigator.
Figure 2:
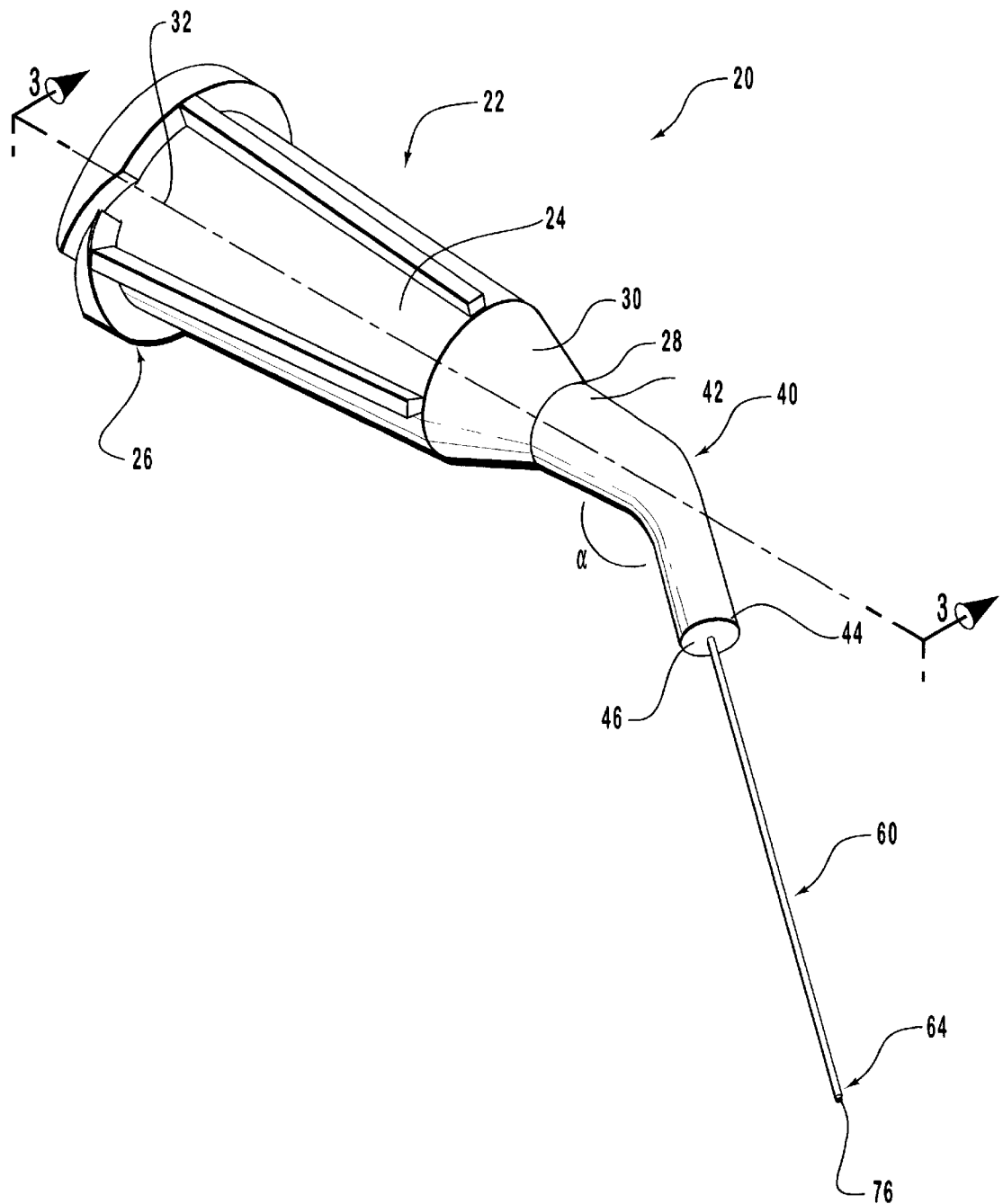
FIG. 2 is a perspective view of one embodiment of an endodontic irrigator tip of the present invention.
Figure 3:
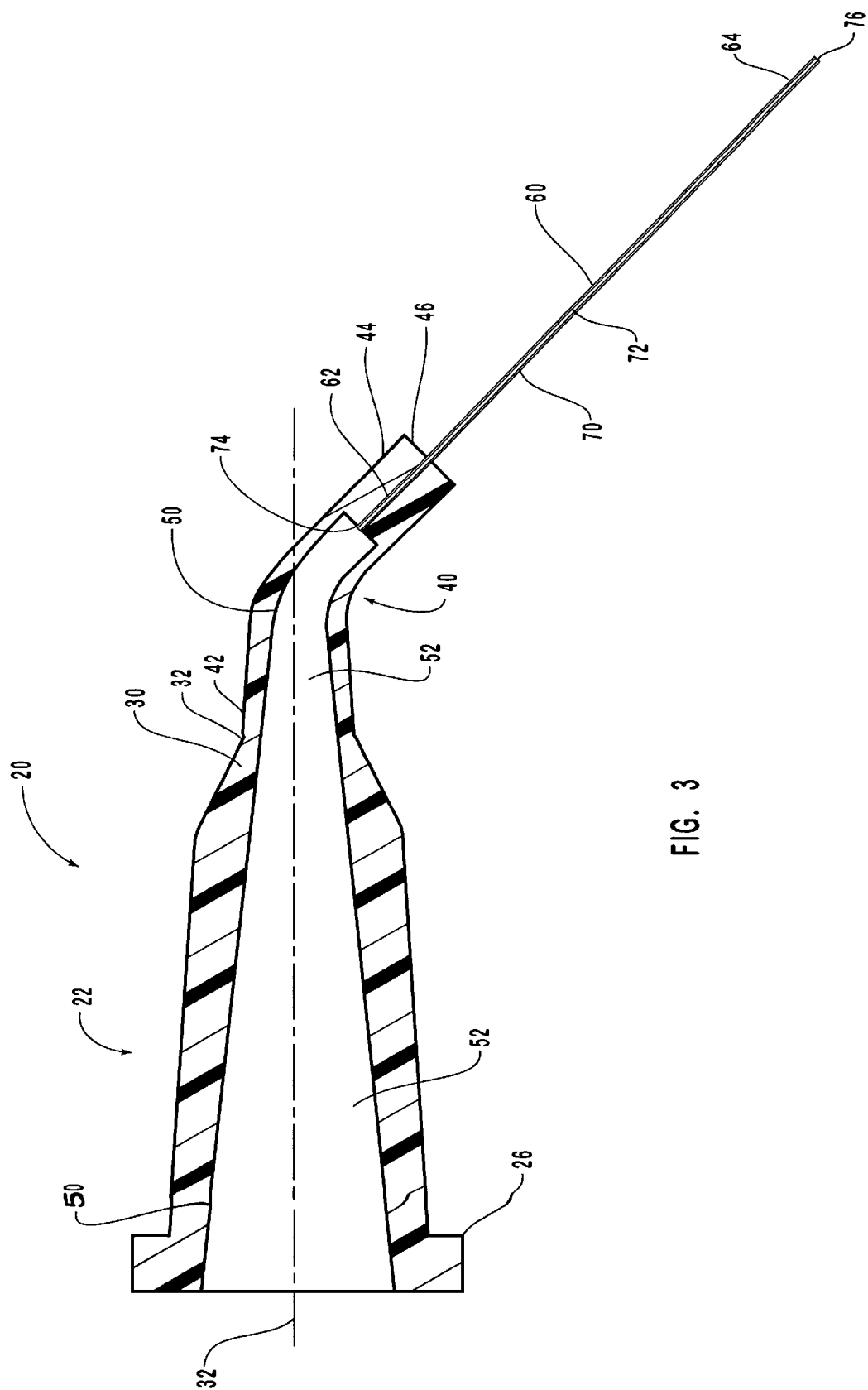
FIG. 3 is a cross sectional view of the embodiment of endodontic irrigation tip of the present invention shown in FIG. 2.

With reference now to FIGS. 2 and 3, an endodontic irrigator tip 20 of the present invention is designed for convenient delivery of a variety of different liquids to a root canal, such as debreeding agents, lubricants, anti-bacterial agents, chelating agents, water, hypochlorites, $H_2O_2$, and EDTA. The primary components of tip 20 are a hub 22, a hollow chamber 52 located within hub 22 and a cannula 60 that extends from hub 22.

Hub 22 has two primary components including body 24 and neck 40. Body 24 and neck 40 are depicted in FIG. 2 as integral components and accordingly body 24 and neck 40 are essentially portions of hub 22. Neck 40 is the portion of hub 22 that is angled. Neck 40 is also preferably narrower than body 24, as depicted. Although body 24 and neck 40 are depicted as integral portions of hub 22, each may also be separate components. Accordingly, body 24 and neck 40 are discussed herein with reference to their respective proximal and distal ends.

Body 24 has a proximal end 26 opposite a distal end 28, the proximal end being the proximal end of hub 22. Body 24 may also include a shoulder 30, which is a tapered portion of body 24, as shown by the embodiment depicted in FIG. 2 at 30. Although shoulder 30 is not necessary, it is preferred as it provides a gradual transition to neck 40. The longitudinal axis of body 26 is identified at 32.

Hub 22 can be coupled to means for delivering fluid to tip 20. Examples of the means for delivering fluid to tip 20 include a syringe, a ratcheting device which increases in pressure upon ratcheting to deliver liquid, or a threaded plunger. Hub 22 further includes means for coupling proximal end 26 of hub 22 to the fluid delivery means, such as male or female Luer lock component, or a standard thread which mates with another thread.

Neck 40 of hub 22 has a proximal end 42 coupled to distal end 28 of body 24. Neck 40 also has a distal stop end 44 opposite proximal end 42 which is the distal end of the hub. Distal stop end 44 has a flat distal face 46. In one embodiment, the length of the neck 40 is in the range of about 3 to about 20 millimeters, more preferably about 4 to about 15 millimeters, and most preferably about 5 to about 12 millimeters.

As shown in FIG. 3, hub 22 has an interior surface 50 within body 24 and neck 40 that defines a hollow chamber 52. Hollow chamber 52 has an inlet 54 that is an opening into hollow chamber 52 for fluid communication with the means for delivering fluid to tip 20. Hollow chamber 52 is an example of a chamber means for containing fluid within hub 22 as received from the means for delivering fluid to the endodontic irrigator tip.

Cannula 60 has a proximal end 62 opposite a distal insertion end 64. Proximal end 62 is sheathed within distal stop end 44 of neck 40 such that a portion of cannula 60 extends from stop end 44 of neck 40 with sufficient length to extend into a root canal of a tooth. Cannula 60 has an outer diameter which permits insertion of cannula 60 into a root canal of a tooth. Additionally, cannula 60 is sufficiently flexible to be advanced within any root canal.

Cannula 60 has an interior surface 70 defining a conduit 72. Fluid enters the conduit 72 from hollow chamber 52 via an inlet 74 located at proximal end 62 such that conduit 72 and hollow chamber 52 are in fluid communication. Fluid exits conduit 72 via outlet orifice 76 at distal insertion end 64, as best viewed in FIGS. 2 and 5*a*. Cannula 60 is an example of a delivery means for delivering fluid from the chamber means to a root canal of a tooth while inserted within the root canal.

Cannula 60 can be coupled to neck 40 in a fluid tight manner through a variety of means. In one embodiment, Cannula 60 comprises a metal material while hub 22 is comprised of polycarbonate or another rigid material. In another embodiment, Cannula 60 extends integrally from hub 22. The gauge of cannula 60 may be, for example, in the range of about 33 to about 22 gauge, more preferably about 31 to about 25 gauge, and most preferably, about 31 to about 27 gauge.

Figure 4:
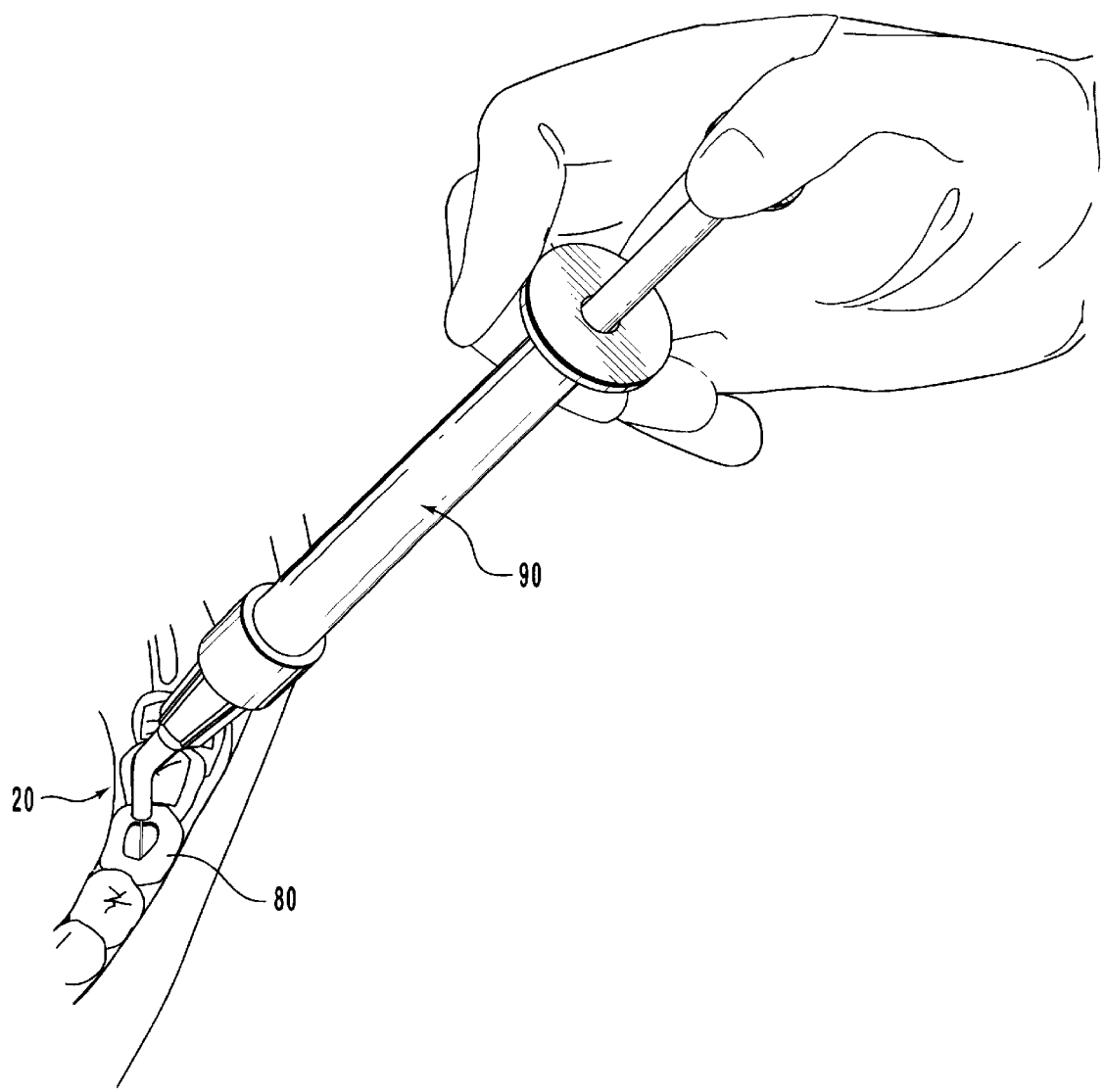
FIG. 4 is a depiction of a practitioner employing the endodontic irrigation tip of FIG. 2, demonstrating the convenience of employing the angled tip of the present invention.
Figure 5:
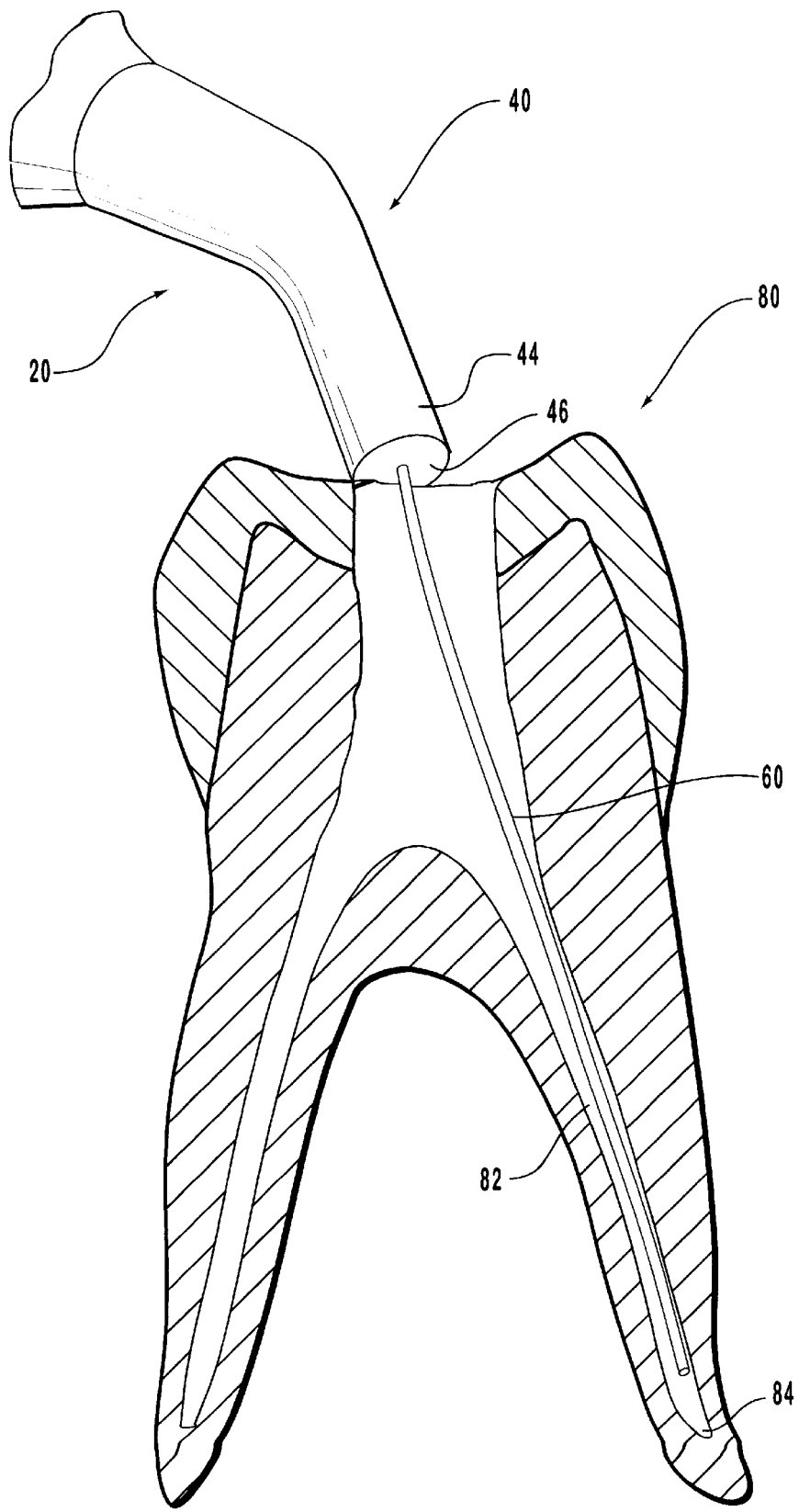
FIG. 5 is a view of a cross section of a tooth which has undergone a root canal procedure and is being irrigated by the endodontic irrigation tip of FIG. 2.

As shown best in FIG. 3, cannula 60 is substantially straight. Since a portion of cannula 60 is sheathed within distal stop end 44 and distal stop end 44 is angled with respect to the longitudinal axis 32 of body 24, cannula 60 is also angled with respect to the longitudinal axis 32 of body 24. Due to the angled configuration, as shown in FIG. 4 and FIG. 5, a practitioner is readily able to place the angled tip 20 into a root canal of a patient's tooth 80 while holding a syringe 90 coupled to tip 20 at an angle with respect to the patient's mouth. This angled configuration enables the practitioner to more easily insert the tip into a root canal and to move the tip within the root canal.

Distal stop end 44 is angled with respect to longitudinal axis 32 at any suitable angle. By way of example, in one embodiment the angle α is in the range of about 45° to about 180°, more preferably, about 60° to about 160°, most preferably, about 90° to about 140°. In the embodiment shown in FIG. 2 and FIG. 3, the angle α is about 120°. The angle preferably enables a practitioner to maneuver the tip without concern for the position of structures other than the tooth being treated. For example, as shown in FIG. 4, tip 20 can be moved while treating tooth 80 without any contact with the teeth on the opposite jaw by the practitioner's hand, syringe 90 or tip 20.

In contrast, use of a tip that is entirely straight requires that the cannula be at least slightly bent while the syringe is generally in contact with the patient's face. Due to this configuration it is difficult to move the syringe other than in a side-to-side fashion along the patient's face or by further flexing the cannula by moving the syringe away from the patient's face. Movement beyond a very limited range can easily result in crimping of the cannula Additionally, a bend in the metal cannula facilitates further crimping when pressure is applied.

Because neck 40 is angled, it is convenient for the practitioner to place cannula 60 within a root canal and to easily move the cannula in any direction. Cannula 60 may be moved in a conical range of motion, a circular range of motion, a side to side range of motion, or any range of motion which is necessary to place cannula 60 in the proper orientation within the root canal. Nevertheless, because of rigid neck 40, the straight and flexible cannula 60 remains substantially straight and is not subject to crimping caused by bending the cannula within the range of motion necessary to move the cannula in order to enable the cannula to irrigate the root canal. This feature of convenience of placement with simultaneous avoidance of crimping of the cannula is a significant advance within the art.

In addition, with reference now to FIGS. 2–4, neck 40 has a substantially greater rigidity than flexible cannula 60. Stop end 44 of neck 40 is sufficiently rigid to ensure that the portion of cannula 60 sheathed within stop end 44 remains substantially straight. Additionally, the rigidity of neck 40 enables the practitioner to direct cannula 60 into a desired area and control the placement of cannula 60 while also preventing the crimping of the portion of cannula ensheathed by neck 40. Thus, although cannula 60 is flexible enough to negotiate the angles of the root canal 82, neck 40 guides cannula 60 precisely into a desired location within the root canal 82. Accordingly, although cannula 60 is flexible, thin and delicate, rigid neck 40 allows the practitioner to precisely guide cannula into a desired position without risking crimping.

In addition, distal stop end 44 of neck 40 has a diameter that is substantially greater than the outer diameter of cannula 60. Thus, as shown in FIG. 4, the stop end 44 acts as an integral stop to prevent penetration into the root canal 82 of endodontic irrigator tip 20 beyond the length of the portion of cannula 60 extending from stop end 44 of neck 40. As shown, the practitioner is able to strategically, conveniently position stop end 44 on the rim of the occlusal surface of a crown and orient cannula 60 in a controlled manner within root canal 82.

As used throughout this specification and the appended claims, the phrase "substantially greater than the outer diameter of the cannula" or a similar phrase refers to a diameter of stop end 44 which is at least about twice as great as the outer diameter of cannula 60. Accordingly, the outer diameter of stop end 44 can, for example, be about 5, 10, 25, 50, etc. times greater than the outer diameter of cannula 60. By way of example, in one embodiment, the diameter of distal stop end 44 of neck 40 ranges from about 0.2 to about 8 millimeters, more preferably about 0.5 to about 5 millimeters, most preferably about 2 to about 4 millimeters.

As shown, flat distal face 46 of stop end 44 is substantially perpendicular to cannula 40. Since face 46 is oriented substantially perpendicular to cannula 60, face 46 can be reliably positioned in a secure manner on the crown of a tooth. The stop prevents apical perforation since only the portion of cannula 60 extending from the stop can be inserted into the root canal, whereas a face with a tapered configuration would slide into pulp chamber 46, thereby allowing perforation of apex 84.

The working length of cannula 60 is the portion of cannula 60 extending past stop end 44 of neck 40. By using an irrigator tip having a cannula with the appropriate working length and a neck 40 having an integral stop end 44, the practitioner is able to avoid apical perforations. In one embodiment, stop end 44 prevents cannula 60 from extending further than within about 1 millimeter above the apex 84, which is desirable in certain procedures. This permits the calculated delivery of fluid all the way to apex 84 without perforating apex 84. Thus, because of stop end 44 and a cannula 60 having an appropriate working length, the practitioner can confidently place cannula 60 in close proximity to apex 84 without perforating apex 84.

In order to provide the appropriate working length for a variety of different root canals, irrigator tips 20 are provided in a kit comprising a plurality of tips having cannulas 60 with different lengths. The advantage of such a kit is that the practitioner is not required to adjust the location of a stop in order to adjust the working length of the cannula, increasing procedure time and potentially introducing contamination due to placing a stop on the cannula. Instead, the working length of each cannula is pre-set and a number of different lengths are provided in each kit. This allows a practitioner to select the precisely desired working length and confidently place the stop end of each tip against the crown of the tooth to act as a stop during the procedure.

In one embodiment, cannula 60 has a working length (i.e., the portion of cannula 60 extending past stop end 44 of neck 40) of about 10 to about 35 millimeters, more preferably about 12 to about 30 millimeters, and most preferably, about 14 to about 28 millimeters. In one embodiment of a kit including tips 20, the working length of each cannula increases incrementally, each working length increasing by about 0.5 mm to about 1 mm. This kit can be used for root canals of all different lengths. Thus, in one kit for example, tips 20 are featured having working cannula lengths of about 10 mm, about 10.5 mm, about 11 mm, and so on up to about 35 mm in increments of one-half a millimeter.

Because the kit features different cannula working lengths, the practitioner can choose the working length of a cannula needed for any root canal procedure, fine tuning the working length of each tip, such that the cannula selected delivers fluid to the precisely desired location. The kit can thus be used in root canals having a variety of different lengths.

As a result of the kit featuring tips having integral stops and preset cannula working lengths, tip 20 does not extend past the apex 84 of root canal, thereby safely irrigating root canal 82. Because of integral stop end 44 and pre-set cannula lengths, the practitioner is not required to place a removable stop on cannula 60. This prevents the potential contamination associated with handling tip 20 while placing a typical removable stop thereon, and acts as a more reliable stop.

Figures 6A, 6B:
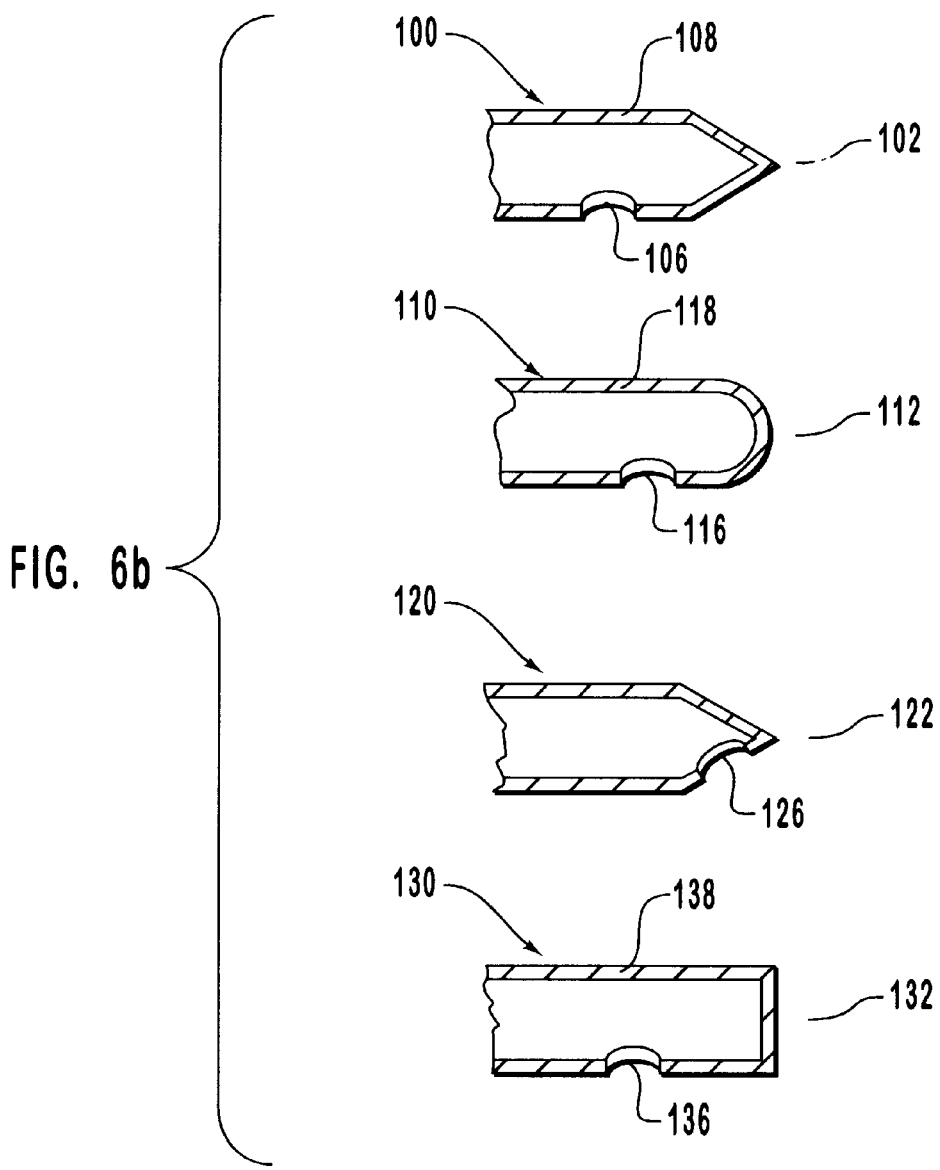
FIG. 6a is an enlarged cross sectional view of the embodiment of the distal insertion end of the present invention shown in FIG. 2.
FIG. 6b is an enlarged cross sectional view of a series of alternate distal insertion ends of the present invention.

FIG. 6a is an enlarged, cross-sectional view of the distal insertion end 64 of cannula 60 shown in FIGS. 2, 3 and 5. In the embodiment depicted in FIG. 6a, distal insertion end 42 includes an orifice 66 for dispelling fluid from syringe 90. This configuration of distal insertion end 64 is advantageous for the practitioner desiring to dispel liquid straight through cannula 60 in a quick and efficient manner. However, as shown in FIG. 6b, a variety of alternative ends may be employed in the present invention.

For example, in the embodiment of the distal insertion end shown at 100, the end terminates at pointed and closed terminal 102 and orifice 106 is located through the wall 108 of the cannula. Orifice 106 is adjacent to terminal 110. End 100 is particularly useful for gently extending the cannula through tissue within root canal 82 before reaching apex 84. Additionally, orifice 106 in wall 108 permits fluid to flow out of the side of the cannula rather than straight as in the embodiment shown in FIGS. 1–5. The location of orifice 106 thus substantially buffers the impact of the flow of liquid which is particularly useful for delivery in the region of apex 84. In addition, orifice 106 is less likely to be clogged by tissue which terminal 102 is pressed through because orifice 106 is located on the side of the cannula.

In the embodiment of the distal insertion end shown at 110, terminal 112 is rounded and closed and orifice 116 is formed through wall 118 of the cannula Orifice 116 is adjacent to rounded terminal 112. End 110 minimizes cutting when the practitioner desires extra precaution in preventing damage to apex 84 or other tissues. End 110 also prevents ledging, a phenomenon caused by tips pressing against a root canal surface until the tip causes a ledge, leading the practitioner to believe that the tip has reached the end of the root canal. End 110 also features delivery from the side of the cannula, substantially buffering the impact of the flow of liquid and preventing clogging.

In the embodiment of the distal insertion end shown at 120, end 120 comprises a sharp, pointed, closed terminal 122 with an orifice 126 formed within a wall of the pointed terminal 122. End 120 is also particularly useful for extending the cannula through tissue within root canal 82 before reaching apex 84 and features precision delivery of fluid in a desired location.

In the embodiment of the distal insertion end shown at 130, terminal 132 is flat and closed and orifice 136 is formed through wall 138 of the cannula. Orifice 136 is adjacent to flat terminal 132. End 130 reduces cutting and also features delivery from the side of the cannula, substantially buffering the impact of the flow of liquid and preventing clogging. End 130 is also efficient to manufacture.

Figure 7:
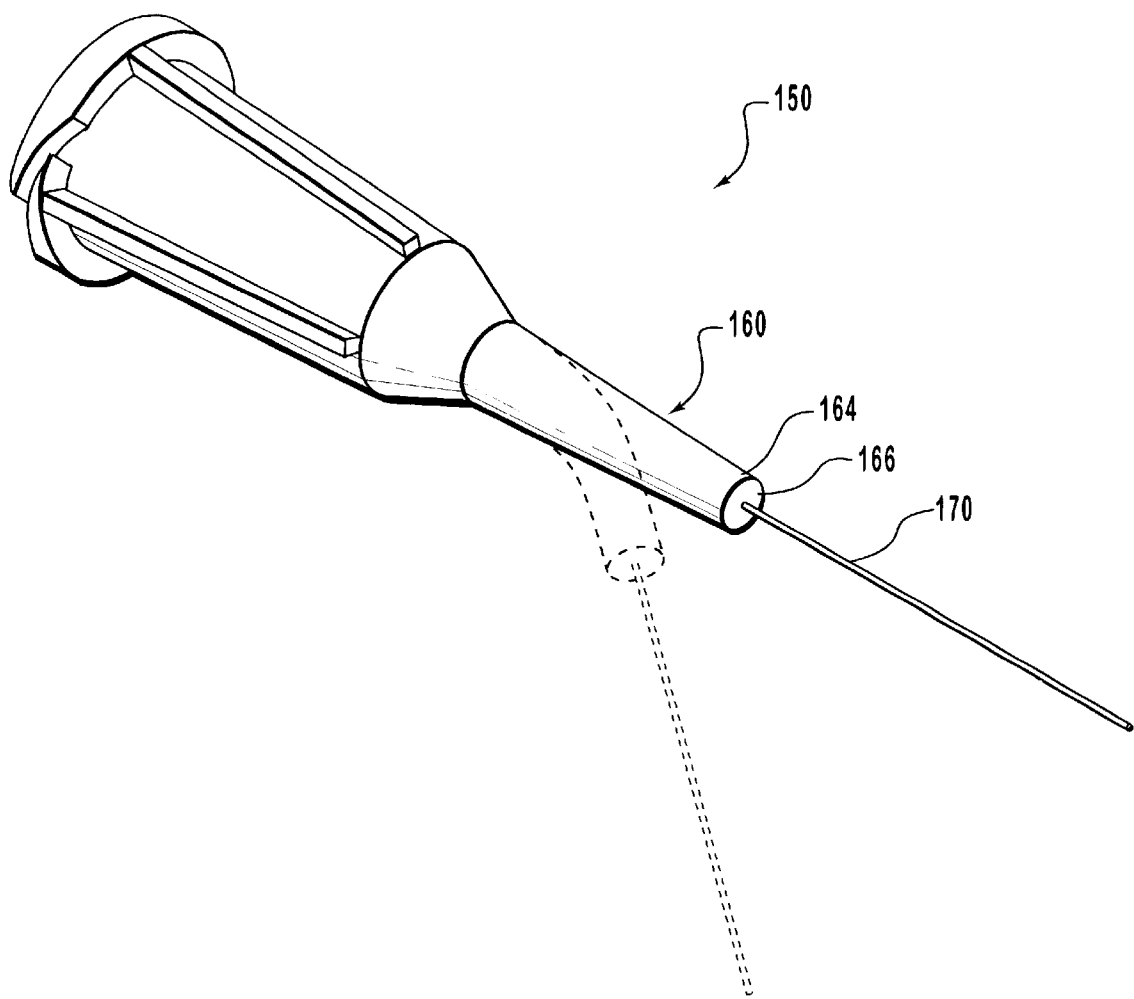
FIG. 7 is a perspective view of another embodiment of the present invention featuring a selectively bendable neck.

While neck 40 is disclosed as being rigid and angled, in one embodiment of an endodontic irrigator tip shown in FIG. 7 at 150, neck 160 can be selectively bent to a desired location by the practitioner, yet is sufficiently rigid to remain in the desired location until bent again by the practitioner.

For example, neck 160 can be formed from a rigid plastic which can become bendable upon heating and then rigid again after subsequent cooling. In one embodiment, the working length of cannula 170 is about 10 to about 35 millimeters, more preferably about 12 to about 30 millimeters, and most preferably, about 14 to about 28 millimeters. Straight tips 150 may also be provided in a kit comprising a plurality of tips having cannulas 170 of different working lengths and/or gauges, such as discussed above with reference to the kit for tips 20. The kit may also comprise a combination of straight and angled tips.

The present invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

What is claimed and desired to be secured by United States Letters Patent is:

1. An endodontic irrigator tip, comprising:
   a hub having a proximal end and a distal stop end opposite the proximal end, the distal end being at an angle with respect to the proximal end;
   chamber means for containing fluid within the hub as received from means for delivering fluid to the endodontic irrigator tip;
   delivery means for delivering fluid from the chamber means to a root canal of a tooth while inserted within the root canal, the delivery means being substantially straight and a portion of the delivery means extending from the distal stop end of the hub such that the delivery means is at an angle with respect to the proximal end of the hub,
      wherein the delivery means has an outer diameter that is substantially less that the diameter of the distal stop end, and wherein the distal stop end has a face that is substantially perpendicular to the delivery means such that the distal stop end of the hub acts as a stop to prevent penetration into a root canal by the delivery means beyond the length of the portion of the delivery means extending from the distal stop end of the hub; and
   means for coupling the proximal end of the hub to means for delivering fluid to the irrigator tip.

2. An endodontic irrigator tip as recited in claim 1, wherein the angle between the proximal end and the distal stop end is in a range from about 45° to about 180°.

3. An endodontic irrigator tip as recited in claim 1, wherein the diameter of the stop end of the hub is in a range from about 0.2 millimeters to about 8 millimeters.

4. An endodontic irrigator tip as recited in claim 1, wherein the hub is sufficiently rigid to ensure that the portion of the cannula sheathed within the distal stop end remains substantially straight.

5. An endodontic irrigator tip as recited in claim 1, wherein a portion of the hub can be selectively bent by a practitioner.

6. An endodontic irrigator tip as recited in claim 1, wherein the angle of the delivery means with respect to the proximal end of the hub enables the delivery means to be moved within a range of motion necessary to irrigate the root canal without crimping the delivery means.

7. An endodontic irrigator tip as recited in claim 1, wherein the delivery means is flexible enough to negotiate the angles of a root canal.

8. An endodontic irrigator tip as recited in claim 1, wherein the portion of the delivery means extending past the distal stop end of the hub has a length in a range from about 10 millimeters to about 35 millimeters.

9. An endodontic irrigator tip as recited in claim 1, wherein the delivery means has a conduit with a gauge in a range from about 33 gauge to about 22 gauge.

10. An endodontic irrigator tip as recited in claim 1, wherein the delivery means is a cannula with a pointed distal tip and an orifice is formed in a wall of the cannula adjacent to the distal tip.

11. An endodontic irrigator tip as recited in claim 1, wherein the delivery means is a cannula with a rounded terminal and an orifice is formed in a wall of the cannula adjacent to the rounded terminal.

12. An endodontic irrigator tip as recited in claim 1, wherein the delivery means is a cannula with a pointed terminal and an orifice is formed within a wall of the pointed terminal.

13. An endodontic irrigator tip as recited in claim 1, wherein the delivery means is a cannula with a flat terminal and an orifice is formed within a wall of the cannula adjacent to the flat terminal.

14. An endodontic irrigator tip, comprising:
   a hub, comprising
      a body having a proximal end, a distal end opposite the proximal end, the body also having a longitudinal axis;
      a neck having a proximal end coupled to the distal end of the body, the neck also having a distal stop end opposite the proximal end, wherein the distal stop end is angled with respect to the longitudinal axis of the body; and
      a hollow chamber defined by an interior surface of the hub, the hollow chamber extending through the body and the neck, the hollow chamber having an inlet that is an opening into the hollow chamber for fluid communication with a means for delivering fluid to the endodontic irrigator tip;
   a substantially straight cannula having a distal insertion end, a proximal end sheathed within the distal stop end of the neck such that the cannula is at an angle with respect to the longitudinal axis of the body and such that a portion of the cannula extends from the stop end of the neck with a length and outer diameter that permits insertion of the cannula into a root canal of a tooth, and a conduit defined by an interior surface of the conduit, the conduit having an inlet located at the proximal end of the cannula and an outlet orifice located at the distal insertion end of the cannula such that the hollow chamber is in fluid communication with the conduit to enable fluid to flow from the hollow chamber through the conduit and exit the outlet orifice,
      wherein the distal stop end of the neck has a diameter that is substantially greater than the outer diameter of the cannula, such that the distal stop end of the neck acts as a stop to prevent penetration into a root canal by the endodontic irrigator tip beyond the length of the portion of the cannula extending from the stop end of the neck; and
   means for coupling the proximal end of the hub to means for delivering fluid to the irrigator tip.

15. An endodontic irrigator tip as recited in claim 14, wherein the distal stop end of the neck is at an angle in a range from about 45° to about 180° with respect to the longitudinal axis of the body.

16. An endodontic irrigator tip as recited in claim 14, wherein the diameter of the stop end of the neck is in a range from about 0.2 millimeters to about 8 millimeters.

17. An endodontic irrigator tip as recited in claim 14, wherein the distal stop end of the neck is sufficiently rigid to ensure that the portion of the cannula sheathed within the stop end remains substantially straight.

18. An endodontic irrigator tip as recited in claim 14, wherein the neck is substantially rigid for guiding the cannula into a desired location within a root canal.

19. An endodontic irrigator tip as recited in claim 14, wherein the angle of the cannula with respect to the longitudinal axis of the body enables the cannula to be moved within a range of motion necessary to irrigate the root canal without crimping the cannula.

20. An endodontic irrigator tip as recited in claim 14, wherein the cannula is flexible enough to negotiate the angles of a root canal.

21. An endodontic irrigator tip as recited in claim 14, wherein the portion of the cannula extending past the distal stop end of the neck has a length in a range from about 10 millimeters to about 35 millimeters.

22. An endodontic irrigator tip as recited in claim 14, wherein the conduit in the cannula has a gauge in a range from about 33 gauge to about 22 gauge.

23. An endodontic irrigator tip as recited in claim 14, wherein the distal insertion end of the cannula comprises a pointed terminal and the orifice is formed in a wall of the cannula adjacent to the terminal.

24. An endodontic irrigator tip as recited in claim 14, wherein the distal insertion end of the cannula comprises a rounded terminal and the orifice is formed in a wall of the cannula adjacent to the rounded terminal.

25. An endodontic irrigator tip as recited in claim 14, wherein the distal insertion end of the cannula comprises a pointed terminal and the orifice is formed within a wall of the pointed terminal.

26. An endodontic irrigator tip as recited in claim 14, wherein the distal insertion end of the cannula comprises a flat terminal and the orifice is formed within a wall of the cannula adjacent to the flat terminal.

27. An endodontic irrigator tip, comprising:
   a hub, comprising
      a body having a proximal end, a distal end opposite the proximal end, the body also having a longitudinal axis;
      a neck having a proximal end coupled to the distal end of the body, the neck also having a distal stop end opposite the proximal end, wherein the distal stop end is angled with respect to the longitudinal axis of the body; and
      a hollow chamber defined by an interior surface of the hub, the hollow chamber extending through the body and the neck, the hollow chamber having an inlet that is an opening into the hollow chamber for fluid communication with a means for delivering fluid to the endodontic irrigator tip;
   a substantially straight cannula having a distal insertion end, a proximal end sheathed within the distal stop end of the neck such that the cannula is at an angle with respect to the longitudinal axis of the body and such that a portion of the cannula extends from the stop end of the neck with a length and outer diameter that permits insertion of the cannula into a root canal of a tooth, and a conduit defined by an interior surface of the conduit, the conduit having an inlet located at the proximal end of the cannula and an outlet orifice located at the distal insertion end of the cannula such that the hollow chamber is in fluid communication with the conduit to enable fluid to flow from the hollow chamber through the conduit and exit the outlet orifice,
      wherein the angle of the distal stop end with respect to the longitudinal axis of the body enables the cannula to be moved within a range of motion necessary to irrigate the root canal without crimping the cannula; and
      wherein the distal stop end of the neck has a diameter that is substantially greater than the outer diameter of the cannula, such that the distal stop end of the neck acts as a stop to prevent penetration into a root canal by the endodontic irrigator tip beyond the length of the portion of the cannula extending from the stop end of the neck; and
   means for coupling the proximal end of the hub to means for delivering fluid to the irrigator tip.

28. An endodontic irrigator tip kit, comprising:
   a plurality of endodontic irrigator tips, each tip comprising:
      a hub having a proximal end and a distal stop end opposite the proximal end;
      chamber means for containing fluid within the hub as received from means for delivering fluid to the endodontic irrigator tip;
      delivery means for delivering fluid from the chamber means to a root canal of a tooth while inserted within the root canal, the delivery means being substantially straight and a portion of the delivery means extending from the distal stop end of the hub such that the delivery means is at an angle with respect to the proximal end of the hub,
         wherein the delivery means has an outer diameter that is substantially less than the diameter of the distal stop end, and wherein the distal stop end has a face that is substantially perpendicular to the delivery means such that the distal stop end of the hub acts as a stop to prevent penetration into a root canal by the delivery means beyond the length of the portion of the delivery means extending from the distal stop end of the hub; and
      means for coupling the proximal end of the hub to means for delivering fluid to the irrigator tip
      wherein the length of the portion of the delivery means extending from the distal stop end of the hub of each of the endodontic irrigator tips is different, enabling the practitioner to treat root canals having different lengths.

29. An endodontic irrigator tip kit, as recited in claim 28, wherein the distal stop end is at an angle with respect to the proximal end of the hub such that the delivery means is at an angle with respect to the proximal end.

* * * * *

UNITED STATES PATENT AND TRADEMARK OFFICE
CERTIFICATE OF CORRECTION

PATENT NO. : 6,079,979
DATED : June 27, 2000
INVENTOR(S) : Francesco Riitano

It is certified that error appears in the above-identified patent and that said Letters Patent are hereby corrected as shown below:

Cover Page, ln 1: before "Irrigator" change "Endonontic" to --Endodontic--

Col. 5, ln. 15: after "body" change "26" to --24--

Col. 7, ln. 18: after "cannula" change "40" to --60--

Signed and Sealed this

Twenty-second Day of May, 2001

*Attest:*

NICHOLAS P. GODICI

*Attesting Officer*     *Acting Director of the United States Patent and Trademark Office*